United States Patent [19]

McKendry et al.

[11] 4,155,746
[45] May 22, 1979

[54] POSTEMERGENT HERBICIDAL METHOD USING 8-SUBSTITUTED BENZOTHIADIAZIONES

[75] Inventors: Lennon H. McKendry; Walter P. Bland, both of Midland, Mich.

[73] Assignee: The Dow Chemical Company, Midland, Mich.

[21] Appl. No.: 926,041

[22] Filed: Jul. 19, 1978

Related U.S. Application Data

[60] Continuation of Ser. No. 790,520, Apr. 25, 1977, abandoned, which is a continuation of Ser. No. 649,178, Jan. 15, 1976, abandoned, which is a division of Ser. No. 497,582, Aug. 15, 1974, Pat. No. 3,940,389, which is a continuation-in-part of Ser. No. 398,139, Sep. 17, 1973, abandoned.

[51] Int. Cl.$^2$ .............................................. A01N 9/14
[52] U.S. Cl. ...................................................... 71/91
[58] Field of Search ........................................... 71/91

[56] References Cited

U.S. PATENT DOCUMENTS

| | | | |
|---|---|---|---|
| 3,041,336 | 6/1962 | Teufel | 260/243 |
| 3,407,197 | 10/1968 | Wright | 71/91 X |
| 3,407,198 | 10/1968 | Wright | 71/91 X |
| 3,708,277 | 1/1973 | Zeidler et al. | 71/91 |
| 3,940,389 | 2/1976 | McKendry et al. | 71/91 X |
| 4,116,672 | 9/1978 | McKendry et al. | 71/91 |

*Primary Examiner*—Joseph Paul Brust

[57] ABSTRACT

Disclosed are certain novel substituted 4(3H)-oxobenzo-2,1,3-thiadiazine-2,2-dioxide compounds and derivatives thereof and methods employing the same in the control of undesired vegetation.

12 Claims, No Drawings

POSTEMERGENT HERBICIDAL METHOD USING 8-SUBSTITUTED BENZOTHIADIAZIONES

CROSS-REFERENCE TO RELATED APPLICATION

The present application is a continuation of our co-pending application, Ser. No. 790,520, filed Apr. 25, 1977, and now abandoned, which is in turn a continuation of our earlier application, Ser. No. 649,178, filed Jan. 15, 1976, and now abandoned, which is in turn a division of our still earlier application, Ser. No. 497,582, filed Aug. 15, 1974 and now U.S. Pat. No. 3,940,389, which is in turn a continuation-in-part of application Ser. No. 398,139, filed Sept. 17, 1973 and now abandoned.

BACKGROUND OF THE INVENTION

In one embodiment, the present invention relates to certain novel substituted 4(3H)-oxobenzo-2,1,3-thiadiazine-2,2-dioxide compounds and derivatives. Another embodiment of this invention relates to the utility of substituted 4(3H)-oxobenzo-2,1,3-thiadiazine-2,2-dioxide compounds as herbicides.

The closest prior art includes U.S. Pat. Nos. 3,041,336 and 3,217,001 which disclose certain 4(3H)-oxobenzo-2,1,3-thiadiazine-2,2-dioxides, bearing single halogen, nitro or loweralkylsulfamoyl substituents in the 6- and 7-phenyl ring positions, which have utility as pharmacological agents. Such prior art does not disclose herbicidal utility. The use of 3-(methylethyl)-1H-2,1,3-benzothiadiazin-4(3H)-one-2,2-dioxide as a herbicide is also known.

An object of the present invention is to provide certain new substituted 4(3H)-oxobenzo-2,1,3-thiadiazine-2,2-dioxide compounds which have good herbicidal properties. Another object of the present invention is to provide a method for controlling unwanted plant growth with substituted 4(3H)-oxobenzo-2,1,3-thiadiazine-2,2-dioxide compounds.

SUMMARY OF THE INVENTION

The present invention is, in one embodiment, directed to novel substituted 4(3H)-oxobenzo-2,1,3-thiadiazine-2,2-dioxide compounds and derivatives corresponding to the formula:

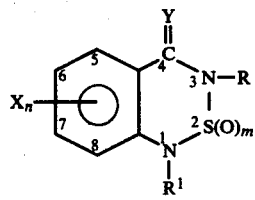

(I)

wherein:
each X independently represents halo, $Y'R^2$, $Y''CF_2C(Z)_3$, $CF_3$, nitro, or loweralkyl, with the proviso that at least one X is always halo or nitro;
n represents an integer of from 2 to 4, inclusive;
m represents an integer of 1 or 2;
R and $R^1$ each independently represent hydrogen, loweralkyl, haloloweralkyl, cycloalkyl, aryl, benzyl, alkenyl, haloalkenyl, alkynyl, haloalkynyl, $-y'R^2$, $-SCCl_3$;

$-\overset{O}{\underset{\|}{C}}NHR^2$, $-NH_2$, $-SO_2aryl$, $-SO_2alkyl$, $-COOR^3$, $-C(CH_3)_2C\equiv CH$ or $-C(CH_3)_2C\equiv N$;
$R^2$ is hydrogen or loweralkyl of from 1 to about 4 carbon atoms;
$R^3$ is loweralkyl;
each Y, Y' and Y" independently represent a chalcogen group having an atomic number of from 8 to 16, inclusive;
each Z independently represents bromo, chloro, fluoro, or hydrogen and, where at least one of R or $R^1$ is hydrogen, the salts thereof with organic or inorganic bases.

In a second embodiment of the present invention, compounds corresponding to Formula I above, except that n is 1, X is a halo or nitro moiety substituted in 8-ring position, all other substituents being as above described, are also claimed. In a third embodiment of the present invention, compounds corresponding to Formula I above, except that n is an integer of from 1 to 4, inclusive, X is halo or nitro when n is 1 and at least one of X is halo or nitro when n is greater than 1, all other substituents being as previously defined, are employed in methods for the control of undesired vegetation. In a further embodiment, certain compounds of the present invention are employed in methods for the selective control of certain vegetation in the presence of desirable crop plants. Such methods comprise applying a herbicidally effective amount of one or more of such compounds to plants and/or their habitats.

For the sake of brevity and convenience, the term "active ingredient(s)" is used hereinafter in this specification to broadly describe the novel substituted 4(3H)-oxobenzo-2,1,3-thiadiazine-2,2-dioxide compounds of Formula I as well as those compounds employed in the method of the present invention.

DETAILED DESCRIPTION

As used in the present specification and claims, the term "herbicide" means an active ingredient which, when used in a growth controlling amount, controls or modifies the growth of undesired plants. By a "growth controlling or effective amount" is meant an amount of compound which causes a modifying effect upon the growth of plants. Such modifying effects include all deviations from natural development, for example, killing, retardation, defoliation, desiccation, regulation, stunting, tillering, and the like. By "plants" it is meant emerging seedlings and established vegetation, including the roots and above-ground portions.

The term "loweralkyl" is used herein and in the appended claims to designate a straight or branched chain alkyl or haloalkyl radical containing, where not otherwise expressly defined, from 1 to about 6 carbon atoms, such as, for example, methyl, ethyl, propyl, isopropyl, butyl, isobutyl, tert-butyl, pentyl, hexyl and the like.

The terms "halo" and "halogen", where employed herein, represent iodine, chlorine, fluorine and bromine. The term "cycloalkyl" is employed to mean radicals containing from 3 to about 8 carbon atoms, such as, for example, cyclopropyl, cyclobutyl, cyclopentyl, cyclohexyl, cyclooctyl and the like. The term "aryl" is employed to mean phenyl or substituted phenyl, such as tolyl and the like. The term "chalcogen" as used herein means those elements of the recognized chalcogen group having an atomic number of from 8 to 16, inclusive, i.e., oxygen and sulfur.

The term "alkenyl" as employed in the present specification and claims designates an alkenyl radical containing from about 3 to about 6 carbon atoms, inclusive, such as, for example, propenyl, 2-methyl propenyl, butenyl, hexenyl and the like which optionally may bear one or more halogen substituents. The term "alkynyl" as used herein and in the appended claims designates an alkynyl radical of from about 3 to about 6 carbon atoms, inclusive, such as, for example, propynyl, 2-methyl propynyl, butynyl, pentynyl, hexynyl and the like which optionally may bear one or more halogen substituents.

The active ingredients of the present invention are normally crystalline solids when substantially pure which are soluble in the usual organic solvents and somewhat soluble in water. The active ingredients of the instant invention are generally useful as herbicides. With respect to compounds of formula I and the use thereof in herbicidal methods, compounds wherein X is selected from the group consisting of halo and loweralkyl of from one to about 2 carbon atoms are preferred. Additionally, compounds wherein n is 2 to 4, X is selected from the group consisting of loweralkyl and halo, R is loweralkyl and halo, R is loweralkyl and $R^1$ is hydrogen also constitute a preferred class. In each of the foregoing preferred embodiments, at least one X is also halo. With respect to compounds where n is 1, X is a halo or nitro moiety substituted in the 8-ring position, X is preferably a halo moiety, with chloro being especially preferred. In all of the foregoing embodiments, compounds wherein R is isopropyl and $R^1$ is hydrogen are further preferred.

The active ingredients of the instant invention can be prepared by cyclizing b-sulphamido carboxylic acid derivatives of the general formula:

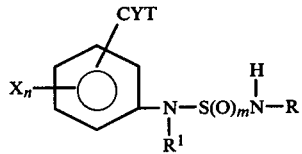

wherein X, n, m, Y, R and $R^1$ are as previously defined and T is a residue which is easily split off such as, for example, a hydroxy, alkoxy or aryloxy or halo group.

In carrying out the preparation of the compounds of the instant invention the selected b-sulphamido carboxylic acid can be cyclized to the desired corresponding active ingredient of the instant invention with a condensing agent. Representative examples of condensing agents include, for example, phosphorous oxychloride, thionyl chloride or aqueous or alcoholic alkaline solutions such as, for example, sodium methylate and the like. The reaction can be carried out under ambient atmospheric pressures and can be conducted in the presence of inert organic solvents such as, for example, benzene, toluene, xylene, higher ethers, halogenated hydrocarbons and the like. While the reactants can be employed in stoichiometric amounts, an excess amount of the condensing agent is preferably employed.

The reaction is usually carried out at temperatures of from about 0° to about 150° C., and usually from about 25° to about 110° C. Preferably, the reaction is carried out by heating the reaction mixture at reflux temperature. The reaction is ordinarily completed in a period of from about 3 to about 24 hours. Following the substantial completion of the reaction, the reaction mixture is cooled, acidified, and the solvent removed in vacuo. The residue thus obtained is extracted with a suitable solvent, such as, for example, carbon tetrachloride, acetone, methylene chloride, chloroform, cyclohexane, or the like, and the extracts combined and cooled to obtain the desired product as a crystalline solid. Alternatively, the solvent is removed prior to acidification and the residue obtained dissolved in water, extracted with ether, and the aqueous layer acidified to a pH of about 1.0 to about 3.0 to precipitate the desired product therefrom. If desired, the recovered product can be further purified by recrystallization from a suitable solvent such as hereinbefore mentioned.

The starting materials of formula II can be prepared according to known methods. Procedures for preparing the same as well as literature references to the same are provided in U.S. Pat. No. 3,041,336. Starting materials of Formula II wherein $R^1$ is hydrogen can, following cyclization as previously set forth, be converted to compounds where $R^1$ is other than hydrogen by reacting the same with typical alkylating, aralkylating, etc., agents such as, e.g., methyl iodide, dimethyl sulphate, ethyl bromide, n-butyl bromide, crotyl bromide, benzyl bromide, and p-bromobenzyl chloride, also the most variously substituted alkyl halides and halides of carbonic acid, carboxylic acids, sulphonic acids and esters, amides and nitriles of halogen carboxylic acids and other types of selected compounds corresponding to the meaning of $R^1$ set forth hereinbefore.

Such reactions can be performed in inert organic solvents such as hydrocarbons, halogenated hydrocarbons, alkanones, the dimethyl ether of ethylene glycol or the like and in the presence of alkali carbonates or bicarbonates. Starting materials of Formula II wherein X represents the $-Y''CF_2C(Z)_3$ moiety are readily prepared by known or analogous procedures disclosed in the literature. For example, starting materials of formula II, wherein X is $-O(S)CF_2CHCl_2$, are readily prepared by sparging 1,1-dichloro-2,2-difluoroethylene into a mixture of sodium methyl hydroxy(thiol)anthranilate in acetone at a temperature of from about 0° to about 10° C. for a period of about 1 to about 2 hours. Following the completion of the reaction, the solvent is removed by evaporation under reduced pressure and the desired starting material recovered.

Those compounds wherein each Z is chloro or bromo are readily prepared by further photochemically halogenating the thus recovered starting material with an appropriate halogenating agent, such as, for example $Cl_2$, ClBr and the like in known procedures using a solvent such as carbon tetrachloride or a heterogenous mixture employing water. Those starting materials wherein Z is fluoro are prepared by reacting the starting materials wherein Z is chloro or bromo with a molten antimony fluoro-chloro compound at temperatures of from about 80° to about 120° C. for periods of ½ to 2 hours.

Other substituents in the 5, 6, 7 and 8 ring positions of the starting materials of Formula II may, depending upon the resistance of such substituent to the preceding reactions, be introduced after cyclization of the same to the corresponding 4(3H)-oxobenzo-2,1,3-thiadiazine-2,2-dioxide compound.

The following examples illustrate the present invention and the manner by which it can be practiced but, as such, should not be construed as limitations upon the overall scope of the same.

EXAMPLE 1

Methyl 5-chloro-3-methyl-2-((((1-methylethyl)amino)sulfonyl)amino)benzoate (26.31 grams; 0.08 mole) was mixed with 200 milliliters (ml) of methanol and sodium methoxide (8.84 grams; 0.164 mole) added thereto. The resulting reaction mixture was heated at the reflux temperature thereof for a period of 5 hours. The solvent was then removed in vacuo leaving a solid brown residue which was dissolved in 200 ml. of water. Sodium bicarbonate (20 grams) was added to the aqueous mixture and the resulting oily layer separated from the aqueous layer. The aqueous layer was acidified with dilute hydrochloric acid and the mixture extracted with ether. The ether extract was reduced in volume by evaporation in vacuo to give a light yellow oil which was dissolved in benzene, dried over anhydrous magnesium sulfate, filtered and evaporated in vacuo to give a light yellow powder. Recrystallization of the powder from methylene chloride and hexane gave the desired 6-chloro-8-methyl-3-(1-methylethyl)-1H-2,1,3-benzothiadiazin-4(3H)-one-2,2-dioxide product as a white crystalline solid having a melting point of 142°–144° C.

Other active ingredients of Formula I are similarly prepared by employing procedures analogous to those set forth in Example 1 above and the foregoing teachings of the specification by cyclizing a selected β-sulphamido carboxylic acid with a condensing agent and are set forth in Table I below:

TABLE I

| Compd. No. | X | Ring Position | R | $R^1$ | Y | m |
|---|---|---|---|---|---|---|
| 2 | Cl | 6,8 | H | $CH_3$ | O | 1 |
| 3 | Br | 6,8 | $-C_4H_9$ | $-C_4H_9$ | S | 2 |
| 4 | F | 5,6,7 | $-CH_2Cl$ | H | O | 2 |
| 5 | I | 5 | $i-C_3H_7$ | $-CH_2Cl$ | S | 1 |
| 6 | Cl | 5,6,7,8 | $-C_4H_8Cl$ | H | O | 2 |
| 7 | 6-Br, 8-Cl | 6,8 | —cyclopropyl | H | O | 2 |
| 8 | 5-Br, 8-$CH_3$ | 5,8 | —cyclohexyl | —OH | S | 1 |
| 9 | 5-Cl, 6,8-di$CH_3$ | 5,6,8 | $-OC_3H_7$ | phenyl | O | 1 |
| 10 | 5-Cl, 6,7,8-tri$CH_3$ | 5,6,7,8 | $-CH_2CH=CH_2$ | $-CH_2CH=CH_2$ | S | 2 |
| 11 | 5,6,7-F, 8-$C_3H_7$ | 5,6,7,8 | $CH_2CH=CH_2$ | $-C_2H_5$ | O | 2 |
| 12 | $-NO_2$ | 6 | $-CH_2CH=CH_2$ | $-NH_2$ | O | 1 |
| 13 | 5,6-di$NO_2$, 8-$CH_3$ | 5,6,8 | $-(CH_2)_4CCl=CXCl$ | H | S | 2 |
| 14 | $-NO_2$ | 5,6,7,8 | $-NH_2$ | cyclohexyl | O | 1 |
| 15 | 5-Cl, 8-$NO_2$ | 5,8 | $-SC_4H_9$ | $-C_4H_8Br$ | S | 2 |
| 16 | 5-Br, 7-$NO_2$, 8-$CH_3$ | 5,7,8 | $-CH_2CH=CH_2$ | H | O | 1 |
| 17 | 6-Cl, 8-$C_4H_7$ | 6,8 | $-CH_2CHClC\equiv CH$ | $-CH_2CH=CH_2$ | S | 2 |
| 18 | 5,6,8-tri$C_2H_5$, 7-Br | 5,6,7,8 | $-OC_2H_5$ | OH | O | 2 |
| 19 | 7-$NO_2$, 8-$C_4H_7$ | 7,8 | benzyl | H | O | 2 |
| 20 | 5-$NO_2$, 6,7,8-triCl | 5,6,7,8 | $-OCH_3$ | $CH_2CH=CHCl$ | S | 1 |
| 21 | 5,6-di$NO_2$, 7,8-di$CH_3$ | 5,6,7,8 | $-SCCl_3$ | H | O | 1 |
| 22 | F | 6,8 | $i-C_3H_7$ | $SCCl_3$ | S | 2 |
| 23 | 5,8-di$C_3H_7$, 7-Cl | 5,7,8 | $SO_2$—phenyl | H | O | 2 |
| 24 | 6-Cl, 8-$CH_3$ | 6,8 | $-SO_2CH_3$ | $-CH_3$ | S | 1 |
| 25 | Br | 5,6,7,8 | $-SO_2C_4H_9$ | $-OCH_3$ | O | 2 |
| 26 | 5-$NO_2$, 6,7,8-triCl | 5,6,7,8 | $COOC_3H_7$ | $-SO_2CH_3$ | S | 2 |
| 27 | 6,8-diCL, 5,7-di$NO_2$ | 5,6,7,8 | $COOC_4H_9$ | H | O | 1 |
| 28 | Cl | 6,8 | $-\overset{\overset{O}{\|}}{C}NH_2$ | $COOCH_3$ | S | 1 |
| 29 | 6-F, 8-$CH_3$ | 6,8 | $\overset{\overset{O}{\|}}{C}NHCH_3$ | $CH_3$ | O | 2 |
| 30 | 6-Cl, 8-$C_4H_9$ | 6,8 | H | $\overset{\overset{O}{\|}}{C}NHC_4H_9$ | O | 1 |
| 31 | 5-Cl, 8-$CH_3$ | 5,8 | $i-C_3H_7$ | $SO_2$-phenyl | S | 2 |
| 32 | 6-$OCF_2CHCl_2$, 8-$NO_2$ | 6,8 | $COOCH_3$ | H | O | 2 |
| 33 | 6-$SCF_2CCl_3$, 8-Cl | 6,8 | $-C_4H_9$ | $CH_3$ | S | 2 |
| 34 | 6,8-diCl, 5-$OCF_2CF_3$ | 5,6,8 | $-SO_2CH_3$ | H | O | 1 |
| 35 | 5-$SCF_2CHBr_2$, 8-Cl | 5,8 | $-CH_2CH=CH_2$ | $NH_2$ | O | 2 |
| 36 | 5,8-di$NO_2$, 6-$OCF_2CHCl_2$ | 5,6,8 | $-\overset{\overset{O}{\|}}{C}NH_2$ | H | S | 1 |
| 37 | 5,6,7-triCl, 8-$OCF_2CH_2Cl$ | 5,6,7,8 | H | $-OCH_3$ | O | 2 |
| 38 | 5-$NO_2$, 6-$SCF_2CCl_3$, 8-$CH_3$ | 5,6,8 | cyclohexyl | $-C_2H_5$ | S | 2 |
| 39 | 5-Cl, 6-$OCF_2CH_3$, 8-$CH_3$ | 5,6,8 | $-COOC_4H_9$ | H | O | 1 |
| 40 | 5-$OCF_2CCl_3$, 6,7,8-triCl | 5,6,7,8 | H | $-C_2H_4Cl$ | O | 2 |
| 41 | 6-Cl, 8-$OCH_3$ | 6,8 | $i-C_3H_7$ | $SCCl_3$ | S | 2 |
| 42 | 5,6-diCl, 8-$CF_3$ | 5,6,8 | $-SO_2C_6H_{13}$ | $-CH_3$ | O | 1 |
| 43 | 5-$NO_2$, 6-$SC_6H_{13}$ | 5,6 | $-COOCH_3$ | $-C_3H_6Cl$ | S | 2 |
| 44 | 5-$NO_2$, 6-Br, 8-$CF_3$ | 5,6,8 | $CH_2CH=CH_2$ | H | O | 2 |
| 45 | 6,8-di$CF_3$, 5-$NO_2$, 7-Cl | 5,6,7,8 | $-CH_3$ | $-SO_2CH_3$ | O | 2 |
| 46 | 5-fl, 6,8-di$OC_3H_7$ | 5,6,8 | $-NH_2$ | $-H$ | S | 1 |
| 47 | 5,7-di$SCH_3$, 8-Cl | 5,7,8 | —benzyl | OH | O | 2 |
| 48 | 5,6,7-triCl, 8-$OCH_3$ | 5,6,7,8 | $-iC_3H_7$ | cyclohexyl | O | 2 |
| 49 | 5-Br, 6-$CF_3$, 8-$OCF_2CHCl_2$ | 5,6,8 | $-C_2H_5$ | $-C_2H_5$ | S | 1 |
| 50 | 5-$NO_2$, 7-n-butoxy | 5,7 | $-OC_3H_7$ | $\overset{\overset{O}{\|}}{C}NH_2$ | O | 2 |
| 51 | 5-$CH_3$, 8-Cl | 5,8 | $-C(CH_3)_2C\equiv CH$ | H | O | 2 |
| 52 | 6-$CH_3$, 8-Cl | 5,8 | $-C(CH_3)_2C\equiv N$ | H | O | 2 |

TABLE I-continued

| Compd. No. | X | Ring Position | R | R¹ | Y | m |
|---|---|---|---|---|---|---|
| 53 | 6-OCF$_2$CHCl$_2$, 8-Cl | 6,8 | —C(CH$_3$)$_2$C≡CH | H | O | 2 |
| 54 | Cl | 8 | i-C$_4$H$_7$ | H | O | 2 |
| 55 | F | 8 | i-C$_3$H$_7$ | H | O | 2 |
| 56 | Cl | 8 | n-C$_3$H$_7$ | H | O | 2 |
| 57 | Cl | 8 | cyclopropyl | H | O | 2 |
| 58 | NO$_2$ | 8 | i-C$_4$H$_7$ | H | O | 2 |
| 59 | NO$_2$ | 8 | sec.-C$_4$H$_7$ | H | O | 2 |
| 60 | NO$_2$ | 8 | n-C$_3$H$_7$ | H | O | 2 |
| 61 | NO$_2$ | 8 | —C$_2$H$_5$ | H | O | 2 |
| 62 | Br | 8 | i-C$_3$H$_7$ | H | O | 2 |
| 63 | Cl | 5 | " | " | " | " |
| 64 | 7-Cl,8-CH$_3$ | 7,8 | " | " | " | " |
| 65 | 5-Cl,8-OMe | 5,8 | " | " | " | " |
| 66 | Cl | 8 | " | " | " | " |
| 67 | NO$_2$ | 8 | " | " | " | " |
| 68 | 5-Cl-8-CH$_3$ | 5,8 | " | " | " | " |

The compounds disclosed in the present invention have been found to be suitable for use in the general post-emergent control of weeds or other unwanted vegetation. Unexpectedly, certain of the active ingredients of the present invention have been found to be active against undesired vegetation in the presence of desired crop plants while producing only a negligible effect on the crop plants. For all such uses, unmodified active ingredients of the present invention can be employed. However, the present invention embraces the use of active ingredients with a material known in the art as an adjuvant in solid or liquid form. Thus, for example, an active ingredient can be dispersed on a finely divided solid and employed therein as a dust. Also, the active ingredients or a solid composition comprising the active ingredients can be dispersed in water, typically with the aid of a wetting agent, and the resulting aqueous suspension employed as a spray. In other procedures, the active ingredient can be employed as a constituent of organic liquid compositions, oil-in-water and water-in-oil emulsions, or water dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

As organic solvents there can be employed hydrocarbons, e.g. benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl Carbitol acetate and glycerine. Mixtures of water and organic solvents, either as solutions or emulsions, can be employed.

The active ingredients can also be applied as aerosols, e.g., by dispersing them in air by means of a compressed gas such as dichlorodifluoromethane or trichlorofluoromethane and other Freons and Genetrons, for example.

The active ingredients of the present invention can also be applied with adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)-ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (nonionic 218), long chain ethylene oxide-propylene oxide condensation products, e.g., Pluronic 61 (molecular weight 1000), polyethylene glycol ester of tall oil acids, sodium octyl phenoxyethoxyethyl sulfate, tris(polyoxyethylene)sorbitan monostearate (Tween 60), and sodium dihexyl sulfosuccinate.

The concentration of the active ingredients in liquid compositions generally is from about 0.0001 to about 95 percent by weight or more. Concentrations of from about 0.0001 to about 50 weight percent are often employed. In dusts or dry formulations, the concentration of the active ingredient can be from about 0.0001 to about 95 weight percent or more; concentrations of from about 0.0001 to about 50 weight percent are often conveniently employed. In compositions to be employed as concentrates, the active ingredient can be present in a concentration of from about 5 to about 98 weight percent. The active ingredient compositions can also contain other compatible additaments, for example fertilizers, phytotoxicants, plant growth regulants, pesticides and the like.

In general treating operations for the modification and control of vegetative growth plants and/or their habitats are contacted with sufficient amounts of a composition containing one or more active ingredients to provide a dosage rate of from about 0.5 to about 20 or more pounds of active ingredient per acre. In selective post-emergent operations in the presence of desired crop plants, the active ingredients are applied at a rate of from about 0.12 to about 2.0 pounds per acre. It is to be understood, however, that all of the active ingredients claimed and compositions containing the same may not be equally effective at similar concentrations against the same plant species. Thus, higher or lower rates than those stated may be necessary in certain instances.

So as to illustrate clearly the phytotoxic properties of the various active ingredients of the present invention, a group of controlled greenhouse experiments is described below.

Various species of plants were planted in beds of good agricultural soil in a greenhouse. After the plants had emerged and grown to a height of about 2-6 inches, a portion of the plants were sprayed with an aqueous mixture, made by mixing a selected active ingredient and emulsifier or dispersant with water, employing sufficient amounts of the treating composition to provide application rates of about 8.0 pounds per acre. Other portions of the plants were left untreated to serve as controls.

After a period of 2 weeks the effect of the test ingredient on the plants was evaluated by a comparison with the control group of plants. As a result of such operations, it was found that a 6,8-dichloro-3-(1-methylethyl)-1H-2,1,3-benzothiadiazin-4(3H)-one-2,2-dioxide test ingredient gave substantially complete control of foxtail, barnyard grass, crabgrass, cotton, pigweed, bindweed and velvet leaf. Of the above plant species, a 7-chloro-3-(1-methylethyl)-1H-2,1,3-benzothiadiazin-4(3H)-one-2,2-dioxide test ingredient was found to substantially control the cotton, bindweed and velvet leaf plants and was substantially inactive against the other plant species. The 6-chloro-3-(1-methylethyl)-1H-2,1,3-benzothiadiazin-4(3H)-one-2,2-dioxide test ingredient similarly gave substantially complete control of the cotton, pigweed, bindweed and velvet leaf plants while giving no control of foxtail, barnyard grass or crabgrass. Of such plant species, a 7-nitro-3-(1-methylethyl)-1H-2,1,3-benzothiadiazin-4(3H)-one-2,2-dioxide test ingredient gave substantially complete control of only pigweeds while being inactive or substantially inactive in the control of the other plant species. An 8-nitro-3-(1-methylethyl)-1H-2,1,3-benzothiadiazin-4(3H)-one-2,2-dioxide test ingredient was found, however to give substantially complete control of foxtail, barnyard grass, crabgrass, cotton, pigweed and velvet leaf.

In selective post-emergent operations employing the above procedures, and low dosage rates of from about ⅛ to about ½ pounds of active test ingredient per acre, it was unexpectedly found that the 6,8-dichloro-3-(1-methylethyl)-1H-2,1,3-benzothiadiazin-4(3H)-one-2,2-dioxide compound gave 100% control of lambsquarter at dosage rates of ½, ¼ and ⅛ pounds per acre, respectively, while affecting cotton plants to the extent of only 15, 5 and 0 percent, respectively, at such rates. In comparative trials, 100% control of lambsquarter was obtained at a dosage rate of ½ pound per acre and 25% and 0% control, respectively, at dosage rates of ¼ and ⅛ pounds per acre, respectively, with the 6-chloro-3-(1-methylethyl)-1H-2,1,3-benzothiadiazin-4(3H)-one-2,2-dioxide compound, which also gave 25%, 15% and 5% control of cotton, respectively, at such dosage rates. Thus, at dosage rates of ¼ lb. or less per acre, the 6,8-dichloro-3-(1-methylethyl)-1H-2,1,3-benzothiadiazin-4(3H)-one-2,2-dioxide compound is clearly superior in activity to the 6-chloro-3-(1-methylethyl)-1H-2,1,3-benzothiadiazin-4(3H)-one-2,2-dioxide compound as it effectively controls lambsquarter with only a negligible effect on cotton, whereas the 6-chloro-3-(1-methylethyl)-1H-2,1,3-benzothiadiazin-4(3H)-one-2,2-dioxide compound gives good control of lambsquarter only at a dosage rate of one-half pound per acre, a dosage rate at which significant damage to cotton is sustained.

In additional comparative operations employing the previously described methods, the 6-chloro-8-methyl-3-(1-methylethyl)-1H-2,1,3-benzothiadiazin-4(3H)-one-2,2-dioxide test compound was found to possess superior activity over that of the 6-chloro-3-(1-methylethyl)-1H-2,1,3-benzothiadiazin-4(3)-one-2,2-dioxide test compound in the control of wild mustard without damage to cotton plants. In such operations the 6-chloro-8-methyl-3-(1-methylethyl)-1H-2,1,3-benzothiadiazin-4(3H)-one-2,2-dioxide compound gave 100% control of wild mustard at dosage rates of one-half, one-fourth and one-eighth pounds per acre, respectively, whereas, the 6-chloro-3-(1-methylethyl)-1H-2,1,3-benzothiadiazin-4(3H)-one-2,2-dioxide compound gave 100%, 25% and 0% control, respectively, at such dosage rates. The 6-chloro-8-methyl-3-(1-methylethyl)-1H-2,1,3-benzothiadiazin-4(3H)-one-2,2-dioxide compound gave 0% damage to cotton at one-eighth and one-fourth pound per acre rates, respectively, and 20% control at a dosage rate of one-half pound per acre. In comparison, the 6-chloro-3-(1-methylethyl)-1H-2,1,3-benzothiadiazin-4(3H)-one-2,2-dioxide compound gave 5, 15 and 25% control of cotton at the same dosage rates. The 6-chloro-8-methyl-3-(1-methylethyl)-1H-2,1,3-benzothiadiazin-4(3)-one-2,2-dioxide compound thus gives complete control of wild mustard with no damage to cotton at rates below one-half pound per acre whereas the 6-chloro-3-(1-methylethyl)-1H-2,1,3-benzothiadiazin-4(3H)-one-2,2-dioxide compound is not effective in controlling wild mustard and produces significant damage to the cotton plants at such rates.

In other similar operations, 5-chloro-8-methyl-3-(1-methylethyl)-1H-2,1,3-benzothiadiazin-4(3H)-one-2,2-dioxide compound was found to give complete control of wild oats and crabgrass at an application rate of about 10 pounds per acre.

In further comparative operations using the foregoing procedures, it was found that the 8-chloro-3-(1-methylethyl)-1H-2,1,3-benzothiadiazin-4(3H)-one-2,2-dioxide compound was found to be selectively superior at low dosage rates over the corresponding respective 6-chloro- and 7-chloro- substituted isomers. In such operations, the application rates necessary to give an average of 70 and 80 percent control of the growth of nine weed plants (Wild mustard, Jimsonweed, Prickly sida, Velvet leaf, Pigweed, Lambsquarter, cocklebur, coffeeweed and Annual morningglory) and a desired crop plant (cotton) were calculated. The results show that the 8-chloro derivative gave an average 70% reduction in weed growth at application rates of about 0.3 pound per acre and an average 80% reduction in growth at a rate of about 0.45 pound per acre. At such respective rates, only 10 and 16% growth reduction of cotton plants was obtained, thus indicating the selectivity of the compound to desired cotton plants. In contrast, the rates necessary to obtain average weed growth reductions of 70 and 80 percent, respectively, were about 1.2 and 2.0 pounds per acre, respectively, for the 7-chloro isomer and about 1.37 and 2.0 pounds per acre, respectively, for the 6-chloro isomer. At such application rates, the 7-chloro isomer was also found to give 36.5% and 50%, respectively, reductions in the growth of desired cotton plants while the 6-chloro isomer likewise was found to give 38.5 and 45 percent, respectively, reductions in the growth of cotton plants, thus indicating that the 7-chloro and 6-chloro isomers are ineffective in giving both good weed control and minimal cotton growth reduction as obtained with the 8-chloro isomer.

Other active ingredients are also found to possess various crop selectivity and weed control properties at various dosage rates.

What is claimed is:

1. A method for controlling undesired plants which comprises applying postemergently to said plants and/or their habitats a herbicidally effective amount in the range of at least about 0.12 to about 20 pounds per acre of a compound corresponding to the formula:

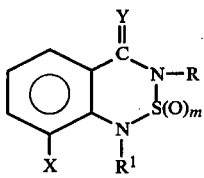

wherein:

X is halo or nitro;

m represents an integer of 1 or 2;

R and $R^1$ each independently represent hydrogen, $C_1$ to about $C_6$ loweralkyl, $C_1$ to about $C_6$ haloloweralkyl, $C_3$ to about $C_8$ cycloalkyl, phenyl, tolyl, benzyl, $C_3$ to about $C_6$ alkenyl, $C_3$ to about $C_6$ haloalkenyl, $C_3$ to about $C_6$ alkynyl, $C_3$ to about $C_6$ haloalkynyl, $-Y'R^2$, $-SCCl_3$,

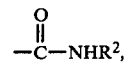

$-NH_2$, $-SO_2$ aryl, $-SO_2$ alkyl, $-COOR^3$, $-C(CH_3)_2-C\equiv N$ or $-C(CH_3)_2C\equiv CH$;

$R^2$ is hydrogen or loweralkyl of 1 to about 4 carbon atoms;

$R^3$ is loweralkyl of 1 to 6 carbon atoms;

each Y and Y' represents a chalcogen group having an atomic number of from 8 to 16 inclusive, and;

where at least one of R or $R^1$ is hydrogen, the salts thereof, with organic or inorganic bases.

2. The method of claim 1 wherein X is halo.

3. The method of claim 1 wherein the compound is applied to the foliage of an existing plant structure.

4. The method of claim 1 wherein the compound is 8-chloro-3-(1-methylethyl)-1H-2,1,3-benzothiadiazin-4(3H)-one-2,2-dioxide.

5. The method of claim 1 wherein the compound is 8-nitro-3-(1-methylethyl)-1H-2,1,3-benzothiadiazine-4(3H)-one-2,2-dioxide.

6. The method of claim 1 wherein the compound is 8-fluoro-3-(1-methylethyl)-1H-2,1,3-benzothiadiazin-4(3H)-one-2,2-dioxide.

7. The method of claim 2 wherein Y is oxygen and m is 2.

8. The method of claim 7 wherein X is fluoro and $R^1$ is $-Y'R^2$ or $-COOR^3$.

9. The method of claim 7 wherein the compound is applied to the foliage of an existing plant structure.

10. The method of claim 6 wherein the application rate is in the range of about 0.12 to about 2 pounds of the compound per acre.

11. The method of claim 8 wherein the application is to the foliage of an existing plant structure.

12. The method of claim 8 wherein the application rate is in the range of about 0.12 to about 2 pounds of the compound per acre.

* * * * *

UNITED STATES PATENT AND TRADEMARK OFFICE
CERTIFICATE OF CORRECTION

PATENT NO. : 4,155,746

DATED : May 22, 1979

INVENTOR(S) : Lennon H. McKendry, et al.

It is certified that error appears in the above-identified patent and that said Letters Patent are hereby corrected as shown below:

Column 3, line 29, delete "also" and insert --always--.

Table 1, Compound No. 13, delete "-$(CH_2)_4$CCl=CXCl" and insert ---$(CH_2)_4$CCl=CCl--.

Compound No. 32, delete "COOCH$_3$" and insert -- -COOCH$_3$--.

Column 10, line 21, delete "thyl)-1H-2,1,3-benzothiadiazin-4(3)-one-2,2-dioxide test" and insert --thyl)-1H--2,1,3-benzothiadiazin-4(3H)-one-2,2-dioxide test--.

Column 10, line 40, delete "thiadiazin-4(3)-one--2,2-dioxide compound thus gives" and insert --thiadiazin-4(3H)--one-2,2-dioxide compound thus gives--.

Signed and Sealed this

Eleventh Day of September 1979

[SEAL]

Attest:

Attesting Officer

LUTRELLE F. PARKER
Acting Commissioner of Patents and Trademarks